United States Patent [19]

George et al.

[11] Patent Number: 4,693,709
[45] Date of Patent: Sep. 15, 1987

[54] SYRINGE

[75] Inventors: Robert D. George, Lake St. Louis; Robert D. Banning, St. Peters, both of Mo.

[73] Assignee: Sherwood Medical Company, St. Louis, Mo.

[21] Appl. No.: 720,825

[22] Filed: Apr. 8, 1985

[51] Int. Cl.⁴ .............................................. A61M 1/00
[52] U.S. Cl. ..................................... 604/212; 604/75; 604/217; 604/218
[58] Field of Search ................. 604/212, 75, 142, 217, 604/218

[56] References Cited

U.S. PATENT DOCUMENTS

| | | | |
|---|---|---|---|
| 2,161,178 | 6/1939 | Lermer | 604/217 |
| 2,514,576 | 7/1950 | Hein et al. | 604/212 |
| 2,727,516 | 12/1955 | Lockhart | 604/212 |
| 2,764,979 | 10/1956 | Henderson | 604/212 |
| 2,848,997 | 8/1958 | Miskel et al. | 604/212 |
| 3,088,634 | 5/1963 | Rosekrans et al. | 604/212 |
| 3,354,883 | 11/1967 | Southerland | 604/212 |
| 3,589,362 | 6/1971 | Zamarra | 128/224 |
| 3,590,722 | 7/1971 | Leptrone | 604/212 |
| 3,635,218 | 1/1972 | Ericson | 604/212 |
| 3,705,584 | 12/1972 | Fript | 604/212 |

FOREIGN PATENT DOCUMENTS

| | | | |
|---|---|---|---|
| 0278032 | 12/1965 | Australia | 604/217 |
| 0532192 | 8/1931 | Fed. Rep. of Germany | 604/212 |
| 0790220 | 2/1958 | United Kingdom | 604/212 |

OTHER PUBLICATIONS

*Pharmaseal,* "Stylex Irrigation Syringes", 1974.
Stylex$^R$ Irrigating Syringes–Pharmaseal, Glendale, Calif., 91201, Feb. 1974, 2 pages.

*Primary Examiner*—Stephen C. Pellegrino
*Attorney, Agent, or Firm*—Stanley N. Garber; Andrew J. Beck; William R. O'Meara

[57] ABSTRACT

An irrigation syringe is provided which includes a barrel having an axially extending annular groove open at the proximal end for receiving the connector portion of a resilient compressible syringe bulb in tight frictional fitting relation. The syringe barrel is adapted to receive, instead of the bulb, a plunger having a piston that may be inserted into the barrel to provide a piston-type syringe so that the barrel can be used either with a syringe bulb or a syringe plunger. The inner wall of the groove has a plurality of slots so that if the syringe barrel is employed as a funnel, liquid will flow from the groove into the barrel.

12 Claims, 4 Drawing Figures ent of the present invention to

SYRINGE

TECHNICAL FIELD

This invention relates to syringes and more particularly to syringes of the type which may be used for medical irrigation purposes.

BACKGROUND ART

Medical irrigation syringes, for example, are often employed for irrigating wounds during surgery, flushing and draining body cavities, and for many other medical purposes.

One type of irrigation syringe is of the bulb-type which includes a syringe barrel and a resilient compressible bulb connected to the syringe and which is squeezed to effect a positive pressure and released to provide a negative pressure within the syringe barrel. The bulb may be formed of a suitable elastomer or plastic and may be either integrally formed with the barrel or formed as a separate member connected to the barrel.

There have been several problems associated with bulb-type syringes. For example, where the bulb and barrel are formed as an integral single-piece unit, the plastic forming the bulg is generally determined by the type of plastic required for the barrel. While such single-piece syringes are economical and useful under many conditions, control of bulb compression and the control of fluid flow is generally not as good as it is with syringes of the type having separate bulb and barrel members. This is because the bulb, when made separately from the barrel, can be formed of a material which is more elastic than that of the barrel and, in general, can provide better compression control. Also, with single-piece syringes, the integral barrel cannot be removed from the bulb so that the barrel cannot be used as a funnel, as is often desired.

Syringes of the type having separately formed bulb and barrel members usually include a bulb having a compressivle bulbous portion connected to a generally cylindrical connector end portion which end portion is connected with the barrel by a tight frictional fit but is usually made to be manually separable from the barrel so that the barrel can be used alone as a funnel. Also, where the bulb and barrel are separable, they are more readily cleaned. However, in some constructions, depending upon the manner in which the bulbous portion is compressed, a fluid leak between the barrel chamber and the atmosphere may occur. This is more apt to happen when the bulb is compressed by squeezing opposed sidewalls of bulb between the thumb and fingers as opposed to when the thumb is used to move the center of the proximal end of the bulb distally. Squeezing the opposed sidewalls tend to pull portions of the connector portion of the bulb radially inwardly away from the barrel wall and tends to cause such a leak. In order to reduce the chance of fluid leaks during compression of the bulb, relatively rigid inserts have been placed in the connector portion of the bulb so that when the bulb is compressed, the relatively rigid supporting insert tends to prevent leakage. Such inserts increase the number of parts, assembly time and cost of the product.

Irrigation syringes of the type that employ a slidable plunger having a piston at the distal end may be employed where positive and negative pressures greater than those obtainable with the bulb-type syringe are required. Syringes of the bulb-type as well as of the piston-type are employed in the medical field for various applications.

SUMMARY OF THE INVENTION

It is therefore and object of the present invention to provide an improved syringe wherein one or more of the above problems are obviated.

Another object is provide a syringe of the bulb-type wherein the bulb may be connected with and removed from the barrel and wherein the chance of undesired fluid leakage when the bulb is compressed is substantially obviated.

Another object of the present invention is to provide a two-piece bulb-type syringe wherein the chance of fluid leakage when the bulb is compressed is substantially obviated and wherein the bulb can be removed from the syringe barrel.

Still another object of the present invention is to provide a syringe of the piston-type having a plunger and barrel wherein the barrel can be used with a syringe bulb or as a funnel.

Still another object is to provide improved single-piece syringe barrel which can be connected either with a syringe bulb or a syringe plunger and wherein when connected with a syringe bulb substantially prevents undesired fluid leakage between the barrel chamber and the atmosphere.

In accordance with one aspect of the present invention, a syringe is provided which inclues a syringe barrel having radially spaced walls defining a groove at the proximal end of the barrel which is open at the proximal end and is adapted to receive a portion of a compressible resilient bulb. A plunger with a piston may be used with the barrel instead of the resilient syringe bulb.

These as well as other objects and advantages of the present invention will become more apparent from the following detail description and accompanying drawings.

DETAIL DESCRIPTION OF THE DRAWINGS

Figure 1:
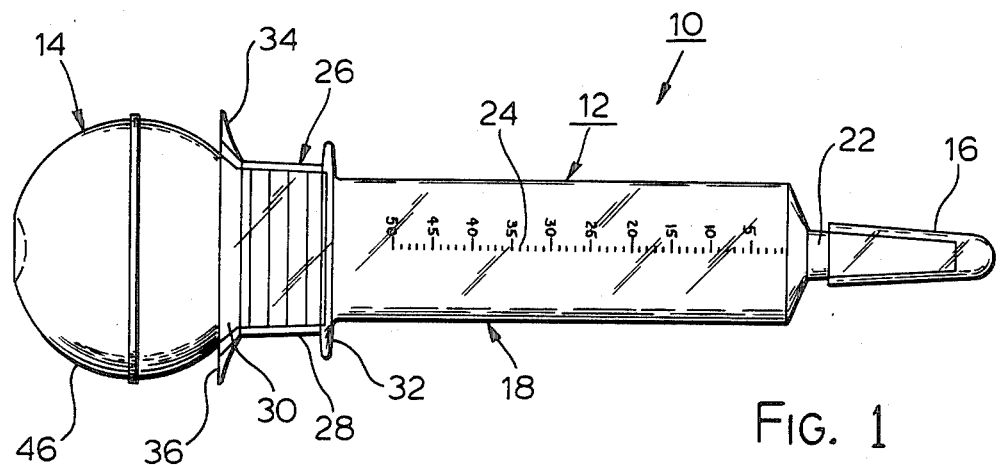
FIG. 1 is a side elevational view of a syringe in accordance with the present invention.
Figure 2:
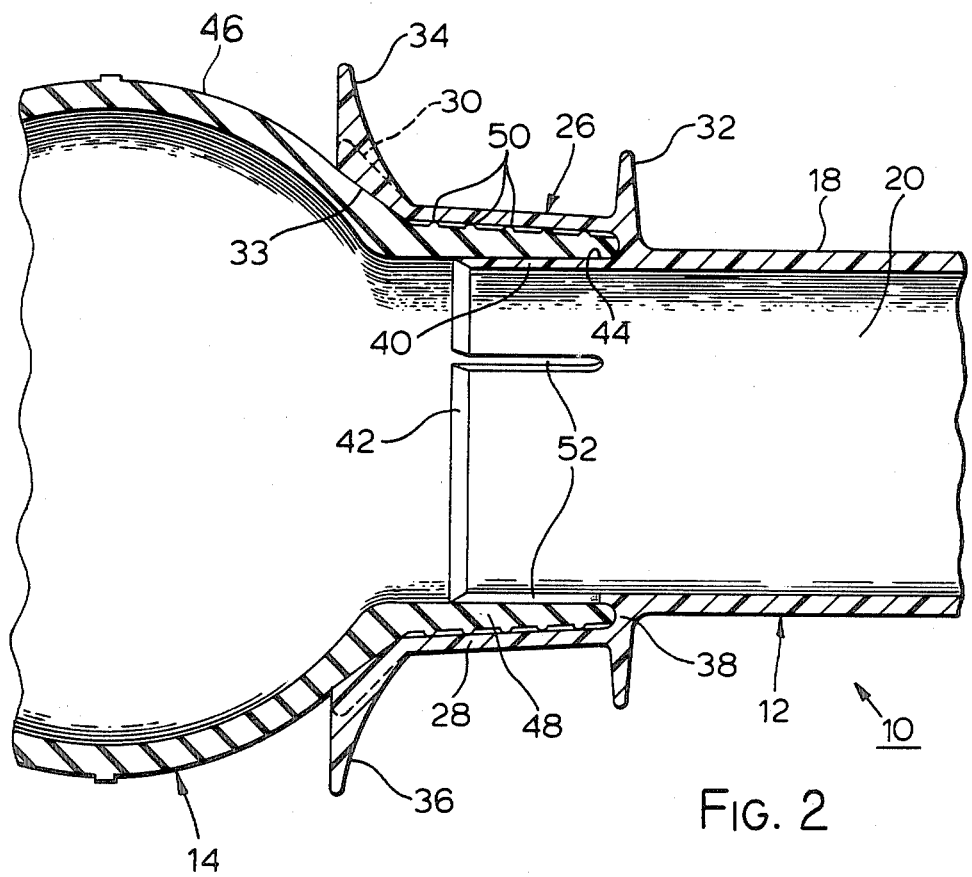
FIG. 2 is an enlarged, fragmentary, longitudinal, cross-sectional view of of the syringe of FIG. 1.

Referring now to the drawings, and more particularly to FIGS. 1 and 2, a two-piece, bulb-type syringe 10 is shown including a syringe barrel 12, and a separate compressible and resilient syringe bulb 14 removably connected in frictional engagement to the proximal end of the barrel 12. Where desired, a closure cap 16 may be connected to close the distal end of the barrel.

Barrel 12 is shown including a cylindrical barrel portion 18 having a cylindrical chamber 20 which tapers radially inwardly at the distal end of the barrel and connects with a hollow, integral syringe tip 22 which frictionally receives cap 16. The barrel 12 is also provided with volumetric indicia indicated at 24. Integrally connected to the proximal end of barrel portion 18 is an annular collar 26 having a generally cylindrical axially extending wall 28 shown having a pair of integral, axially spaced annular flanges 30 and 32. Flange 30 has an inner generally conical surface 33 tapering radially outwardly in the proximal direction and a pair of diametrically disposed radially outwardly extending finger tabs 34 and 36. Wall 28 and flange 32 are connected by an integral radially inwardly extending annular wall 38 to barrel portion 18. The cylindrical wall 28 is generally concentric with and spaced radially outwardly of the proximal end portion, indicated at 40, of barrel portion 18 and extends proximally beyond the proximal end wall, indicated at 42, of the barrel portion 40.

The inner surface of collar wall 28 and the outer surface of the proximal end portion 40 of the barrel portion 18 are radially spaced to define an annular groove 44 (FIG. 2) open at the proximal end and closed at the distal end by wall 38. The inner surface of wall 28, and therefore, groove 44, are slightly tapered radially outwardly and proximally to readily receive a portion of the bulb 14 in tight frictional engagement, as will be discussed hereafter.

Bulb 14 includes a resilient compressible bulbous portion 46 and an integral generally cylindrical end connector portion or sleeve 48 shown frictionally disposed in the groove 44 of barrel 12. Sleeve portion 48 of the bulb is provided with a plurality of axially spaced integral sealing rings 50 which resiliently engage the inner surface of wall 28 of the collar 26. Bulb 14 can be removed from and inserted into the groove 44 as desired. The sleeve portion 48 is shown in frictional engagement with the opposed facing walls 28 and 40 of the groove 44. The inner diameter of sleeve portion 48 is greater than that of bore 20 and less than that of wall of 28. A portion of the bulbous portion 46 adjacent sleeve 26 generally conforms in shape and engages tapered wall 33 providing a good supporting fit between the bulb and barrel.

It is sometimes desired to remove the bulb 14 and employ the barrel 12 as a funnel. For example, the barrel may be used for transferring liquid, such as from a container to a selected area of the patient. To avoid trapping fluid in groove 44, whenever the barrel 12 is used as a funnel, a plurality of longitudinally extending slots 52 are provided in the wall portion 40 so that any fluid entering the groove 44 from the open proximal end of the barrel will flow through the slots 52 and into bore 20. Three equally circumferentially spaced slots 52 are shown (FIG. 4).

The syringe 10 may be operated to produce a positive or negative pressure in bore 20. With the cap 16 removed, the bulb 14 may be, for example, compressed by placing two fingers under the annular flange 30 or 32, preferably under tabs 32 and 34, and pressing the thumb in the center of the proximal end wall of the bulb 14 to move the proximal wall distally compressing or collapsing the bulb 14 to effect, for example, the discharge of air from the bore 20 and the bulb, the air flowing out of the tip 22. While holding the bulb compressed, the syringe tip 22 may be inserted into a fluid such as a liquid solution and the pressure of the thumb on bulb 14 released so that the resiliency of the bulb 14 returns the bulb to its uncompressed or normal bulbous shape creating a negative pressure within the bore 20 so that liquid is drawn into the bore and bulb. The liquid, of course, can be discharged out through tip 22 by again compressing bulb 14.

In pressing the center of the proximal wall of the bulb with the thumb as described, the bulb and sleeve portion 48 tend to be urged even further into the groove 44 and into tight engagement with the opposed walls 28 and 40 of the groove. Instead of compressing the bulb 14 by using the thumb as described, some persons pinch the opposed sidewalls of the bulbous portion 46 between the thumb and the index finger to thereby move the opposed sidewalls of the bulb toward each other. When the bulb 14 is compressed in the latter manner, integral walls 28 and 40 of the groove 44 serve to prevent the sleeve portion 48 of the bulb from distorting and causing leakage of air between the bulb and the atmosphere. The wall portion 40 prevents parts of the sleeve portion 48 from moving inwardly away from the wall 28 during compression of the bulb.

Figure 3:
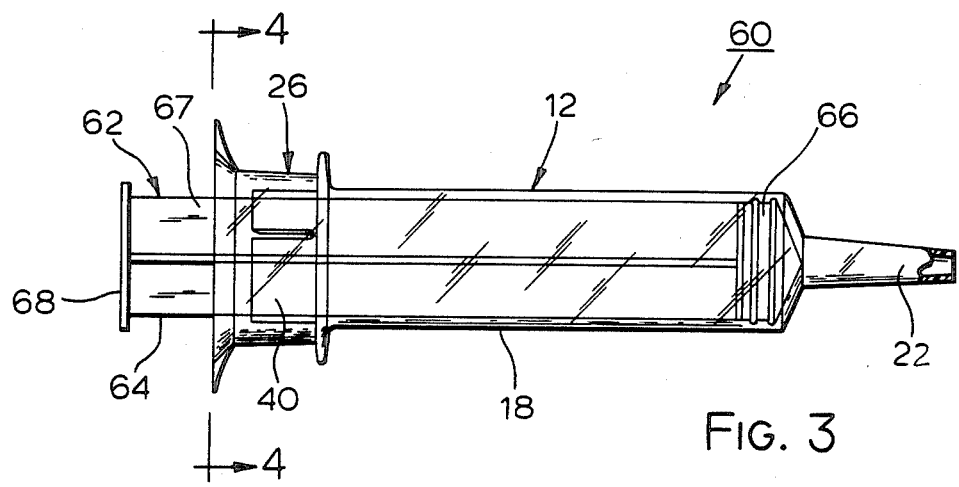
FIG. 3 is a syringe of the piston-type in accordance with another embodiment of the present invention and which employs the barrel of FIG. 1.
Figure 4:
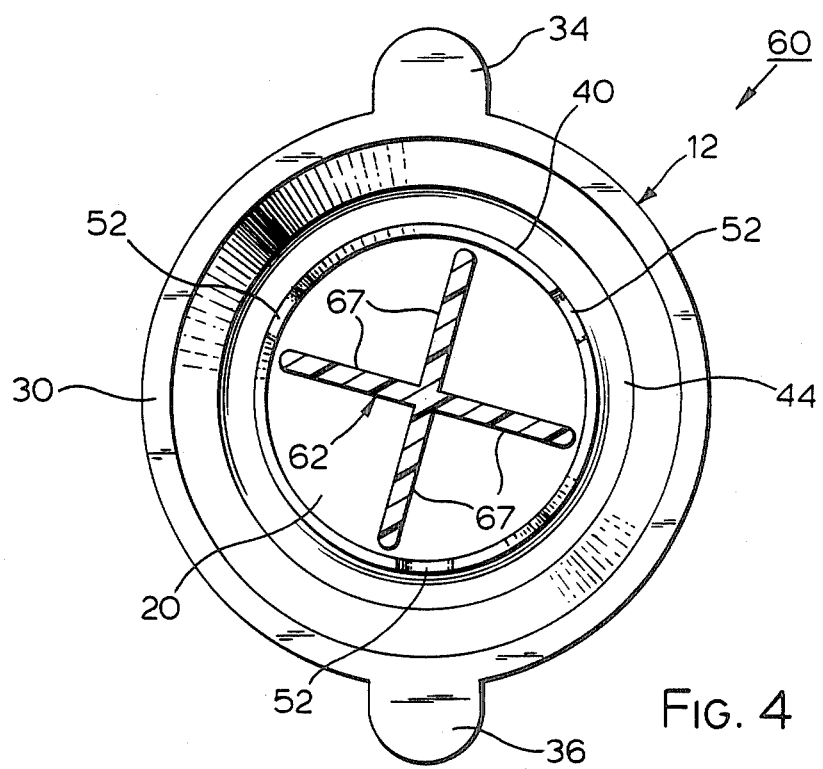
FIG. 4 is an enlarged cross-sectional view taken along the line 4—4 of FIG. 3.

The syringe shown at 60 in FIGS. 3 and 4 is of the piston-type and includes the syringe barrel 12 of FIG. 1 and by a plunger 62 shown extending within the bore 20 of the cylindrical portion 18 of the barrel. Plunger 62 may be any suitable or conventional plunger and is shown including a elongate piston rod 64 having a slideable sealing piston 66 such as formed of a suitable rubber or other elastomeric material. Piston rod 66 is shown formed of four walls 67 circumferentially spaced. At the proximal end of the piston rod is an enlarged head indicated at 68 which may be grasped by the hand during movement of the plunger 62 longitudinally within the bore 20 of barrel 12. As is well known, movement of the plunger 62 proximally relative to the barrel 12 produces a negative pressure within the bore 20 which may be used for suctioning purposes. Movement of the plunger distally relative to the barrel 12 will of course cause positive pressure or discharge of fluid in bore 20 through the syringe tip 22 and externally of the barrel.

The effective diameter of the piston rod 64, that is, in this case, the diameter of a circle tangent to the radially outer end of the four walls 67, is slightly less than the inner diameter of bore 20 so that the plunger is prevented from excessive wobble or excessive lateral movement during controlled longitudinal or axial movement of the plunger during use. Excessive wobble tends to interfere with the control of the movement of the plunger. The proximal end portion 40 of the barrel 12 tends to limit the lateral movement or "play" of the piston rod 64, and is especially effective in maintaining the piston rod in general alignment as the piston 66 approaches the proximal end of the barrel 12. The proximal end wall 42 is tapered radially inwardly and distally so as to facilitate the insertion of pistion 66 when inserted into the proximal end of the barrel 12.

The barrel 12 may be formed of any suitable material, such as glass or plastic, and preferably it is formed (as shown) of a transparent thermoplastic material, such as polypropylene. The cap 18 may of course be formed any suitable material such as a suitable rubber, or plastic, such as polypropylene. The piston rod 52 may also be formed of any suitable relatively rigid material, such as a suitable plastic, for example, polypropylene. The bulb 14 may of course be made of any suitable resilient, compressible material such as natural rubber, a suitable synthetic rubber, or plastic or elastomeric material commonly used in the art for making syringe bulbs.

By providing cylinder 12 with an annular groove open at the proximal end for receiving the generally cylindrical portion 48 of the bulb, the bulb can be compressed in the normal way in either typical manner, that is by pressing the thumb on the proximal end or pinching the opposed sidewalls toward each other without causing unintended fluid leakage from the barrel or interior of the bulb to the atmosphere. The same barrel 12 can be used in a highly satisfactory manner when it is desired to use either a plunger, such as plunger 62, or a bulb, such as bulb 14 as the pressure generating member. Thus, a substantial economy is obtained since the same mold can produce like barrels, such as barrel 12 that can be employed in either the bulb-type syringe, such as syringe 10, or in the piston or plunger-type syringe, such as syringe 60. Good results are obtained with both types of syringes 10 and 60. Furthermore, the barrel 12 can be used alone as a funnel and, as mentioned, fluid can flow through slots 52 and into the bore 20.

As various changes could be made in the above described constructions without departing from the scope of the invention, it is intended that all matter contained in the above description shown in the accompanying drawings be interpreted as illustrative and not in a limiting sense.

What is claimed is:

1. An irrigation syringe barrel device comprising an integral single piece barrel including a cylindrical portion having a cylindrical bore open at the proximal end thereof and capable of receiving a sryinge plunger rod having a piston thereon slidable longitudinally in sealing engagement with the walls of said bore for generating fluid pressure in said bore, an integral syringe tip at the distal end of said cylindrical portion in fluid communicaion with said bore, integral axially extending collar means at the proximal end of said cylindrical portion, and a radially inwardly extending integral wall portion integrally connecting the distal end of said collar means with said cylindrical portion at a point distally of the proximal end of said cylindrical portion and with the radially inner surface of said collar means in radial spaced relation with the radially outer surface of said cylindrical portion, said inner surface of said collar means and said outer surface of said cylindrical portion defining an axially extending substantially annular groove open at the proximal end thereof, said groove being capable of receiving a cylindrical end portion of an elastomeric syringe bulb in tight fitting engagement with said inner surface of said collar means and said outer surface of said cylindrical portion.

2. The device of claim 1 wherein said inner surface of said collar means at the proximal end thereof has a generally conical surface tapering radially outwardly in the proximal direction for supporting engagement with an outer surface of a syringe bulb when the end portion of the bulb is received in said groove, said conical surface being proximal of the proximal end of said groove.

3. The device of claim 1 further including an elastomeric syringe bulb having a bulbous portion and a generally cylindrical integral end portion connected to the bulbous portion, the distal end portion of said bulbous portion engaging said inner surface of said collar means and said integral end portion of said bulb engaging said outer surface of said cylindrical portion of said barrel when said integral end portion of said bulb is received in said annular groove, said integral end portion of said bulb being removable from said groove.

4. The device of claim 1 wherein said collar means includes a pair of axially spaced, radially outwardly extending integral flanges adjacent the proximal end thereof.

5. The device of claim 1 further including a syringe plunger including a piston rod and an elastomeric piston both axially movable in said bore for generating fluid pressure within said bore.

6. The device of claim 1 wherein said collar means extends proximally beyond the proximal end of said cylindrical portion.

7. The device of claim 1 wherein said cylindrical portion has a plurality of axially extending slots adjacent the proximal end thereof effecting fluid communication between said groove and said bore for allowing liquid that may enter said groove during use of said barrel as a funnel to flow from said groove to said bore.

8. The device of claim 1 wherein the inner diameter of said collar means is greater than the outer diameter of said cylindrical portion at said groove and the device includes a syringe having a bulbous portion and a cylindrical portion insertable in said groove.

9. The device of claim 7 wherein said conical surface connects with said inner surface of said collar means and said groove.

10. The device of claim 1 including radially outwardly extending flange means integral with said collar means and proximally of said groove.

11. The device of claim 10 further including second radially outwardly extending flange means distally of said groove.

12. The device of claim 1 wherein said bore extends proximally beyond the distal end of said groove.

* * * * *